United States Patent [19]

Kidd et al.

[11] Patent Number: 4,554,336
[45] Date of Patent: Nov. 19, 1985

[54] URETHANE MODIFIED ORTHODONTIC ADHESIVE

[75] Inventors: Patrick D. Kidd, San Dimas; Terry L. Sterrett, Long Beach, both of Calif.

[73] Assignee: Sybron Corporation, Rochester, N.Y.

[21] Appl. No.: 546,472

[22] Filed: Oct. 28, 1983

[51] Int. Cl.$^4$ .................. C08F 26/02; C08F 126/02; C08F 226/02
[52] U.S. Cl. ..................................... 526/301; 523/109
[58] Field of Search ........................................ 526/301

[56] References Cited

U.S. PATENT DOCUMENTS

| | | | |
|---|---|---|---|
| 3,825,518 | 7/1974 | Foster | 526/301 |
| 3,891,523 | 6/1975 | Hisomatsu et al. | 526/301 |
| 3,907,865 | 9/1975 | Miyata et al. | 526/301 |
| 4,271,223 | 6/1981 | Lambert et al. | 526/301 |
| 4,380,432 | 4/1983 | Orlowski et al. | 523/118 |
| 4,394,494 | 7/1983 | Miyake et al. | 526/301 |

*Primary Examiner*—Joseph L. Schofer
*Assistant Examiner*—Peter F. Kulkosky
*Attorney, Agent, or Firm*—Robert A. Gerlach; Owen D. Marjama

[57] ABSTRACT

A trifunctional methacrylate or acrylic terminated urethane resin of the following chemical structure:

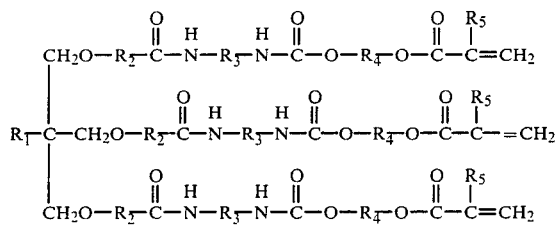

Where:
$R_1$ is —H, —CH$_3$, —CH$_2$CH$_3$, or —CH$_2$CH$_2$CH$_3$,
$R_2$ is (—CH$_2$CH$_2$—O—)$_n$ or

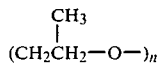

where: n=2 to 10,
$R_3$ is a divalent organic radical obtained by removal of two isocyanato groups from an organic diisocyanate,
$R_4$ is methylene, ethylene or propylene, and
$R_5$ is —H, or —CH$_3$.

3 Claims, No Drawings

URETHANE MODIFIED ORTHODONTIC ADHESIVE

BACKGROUND OF THE INVENTION

The existence of residual dental adhesive subsequent to the debonding of dental appliances, such as an orthodontic bracket, has long been a problem to the orthodontist. The presence of such residual adhesive may lead to the injury of the tooth's enamel surface when abrasive or mechanical methods are used to remove the existing residual adhesive. There has, therefore, been a continuing need for an adhesive system or adhesive bonding technique which will yield a preferential bond to the metallic faying surface, yet which will still maintain a strong, environmentally durable bond between the adherends. Such a technique should yield an adhesive failure between the tooth's enamel surface and the adhesive, thus allowing the adhesive to be carried off by the dental appliance.

In the past, various approaches have been taken to alleviate the aforementioned problems. Such techniques attempt to increase the preference of adhesive bonding to the metallic faying surface through mechanical and chemical techniques. For example, chemical and photochemical etching of the metallic faying surface have been tried as a promoter of preferential bonding to metallic adherend. Other approaches have included the use of different dental appliance geometries or the use of epoxy or bis-GMA based adhesives. All of the previously mentioned techniques have met with marginal success for various reasons. For example, the technique of etching is too cumbersome with respect to processing, whereas the use of epoxy and bis-GMA based adhesive resins failed in a brittle manner, leaving adhesive behind on the tooth's enamel due the presence of the aromatic moiety of the monomer backbone.

Urethane monomers and oligomers which are terminated with readily polymerizable acrylic or methacrylic functional groups have been previously employed in order to strengthen or toughen composite dental filling materials, as shown in U.S. Pat. Nos. 4,110,184; 4,089,763; 3,862,920 and 3,825,518. The compounds which have been used were based on backbone structures which are essentially linear. The linear structure of these molecules basically matched the linear structures of the commonly used dimethacrylate resins in dental composite restoratives and orthodontic adhesives such as Bis/GMA or ethoxylated Bis/GMA or reactive diluents such as triethylene glycol dimethacrylate, as taught by U.S. Pat. Nos. 3,751,399; 3,730,947 and 3,792,531. Trifunctional monomers having non-linear structural characteristics have been employed as additives to increase cross-linking density, (U.S. Pat. No. 3,835,090) but it was observed that the incorporation of long aliphatic chains (C>4) would cause undesired softening of the resulting binder resin.

SUMMARY OF THE INVENTION

In order to alleviate the aforementioned problems associated with prior art dental adhesives, an adhesive system was developed which preferentially bonds to the metallic faying surface, yet still maintains a strong environmentally durable bond which will fail in a ductile fashion. It was discovered that a trifunctional methacrylate or acrylic terminated urethane resin with non-linear structure would toughen the binder resin of an orthodontic adhesive or dental composite, lowering the modulus of elasticity and increasing strain at failure without reducing ultimate strengths.

Such an adhesive system increases the bond strength, while failing in a ductile fashion, hence leaving essentially no adhesive behind on the tooth's surface. This is accomplished by two modes of action on the part of adhesive. The first being an increased amount of primary tack in the adhesive, with such a characteristic yielding a preferential bonding for the metallic faying surface via the cyano modieties of the urethane. Secondly, the presence of the urethane in the polymer network of the polymerized adhesive causes a shift in the mode of failure of the adhesive from one which is primarily brittle to one which is primarily ductile. Such a transition from a brittle mode of failure to a ductile mode of failure results in a decrease in the presence of residual adhesive on the tooth's surface subsequent to debonding.

The compounds of this invention have the following structure:

$$\begin{array}{c}
CH_2O-R_2-\overset{O}{\overset{\|}{C}}-\overset{H}{N}-R_3-\overset{H}{N}-\overset{O}{\overset{\|}{C}}-O-R_4-O-\overset{O}{\overset{\|}{C}}-\overset{R_5}{\overset{|}{C}}=CH_2 \\
| \\
R_1-\overset{}{C}-CH_2O-R_2-\overset{O}{\overset{\|}{C}}-\overset{H}{N}-R_3-\overset{H}{N}-\overset{O}{\overset{\|}{C}}-O-R_4-O-\overset{O}{\overset{\|}{C}}-\overset{R_5}{\overset{|}{C}}=CH_2 \\
| \\
CH_2O-R_2-\overset{O}{\overset{\|}{C}}-\overset{H}{N}-R_3-\overset{H}{N}-\overset{O}{\overset{\|}{C}}-O-R_4-O-\overset{O}{\overset{\|}{C}}-\overset{R_5}{\overset{|}{C}}=CH_2
\end{array}$$

Where:
$R_1$ is $-H$, $-CH_3$, $-CH_2CH_3$, or $-CH_2CH_2CH_3$,
$R_2$ is $(-CH_2CH_2-O-)_n$ or $$\begin{array}{c} CH_3 \\ | \\ (CH_2CH_2-O-)_n \end{array}$$

where: n=2 to 10,
$R_3$ is a divalent hydrocarbon radical, obtained by the removal of the isocyanato groups from a divalent isocyanate. Suitable diisocyanates contain from four to 16 carbon atoms and can be aromatic, aliphatic or cycloaliphatic. Typical examples of $R_3$ are:

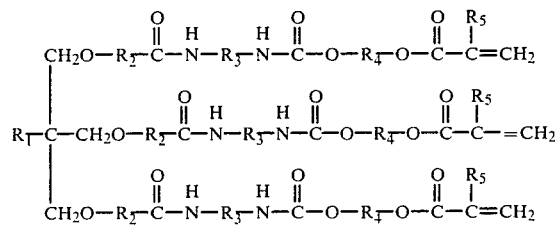

$-CH_2CH_2-CH_2-CH_2-$, $+CH_2)_6$ $R_4$ is $-CH_2-$, $-CH_2CH_2-$, or $-CH_2CH_2CH_2-$,
$R_5$ is $-H$, or $-CH_3$.

The preferred structure is one in which:
$R_1 = -CH_2CH_3$
$R_2 = (CH_2CH_2-O-)_5$
$R_3 =$ 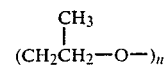

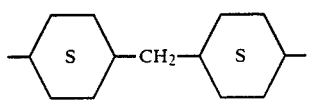

$R_4 = -CH_2CH_2-$
$R_5 = -CH_3$

Throughout the specification and claims by the symbols

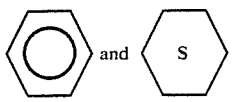

is meant benzene and cyclohexane rings respectively.

The composition set forth above may be prepared by initially reacting a triol such as for example trimethylolpropane with ethylene oxide, propylene oxide, ethylenechlorohydrin or propylenechlorohydrin to form a polyether adduct having a weight average molecular weight of from about 400 to about 2,000. This adduct in turn is reacted with an organic diisocyanate such as, for example, 4,4' diphenylmethane diisocyanate, 2,4-tolylene diisocyanate, 1,5-phenylene diisocyanate, 2,6-tolylene diisocyanate methylene bis(4-cyclohexylisocyanate), tetramethylene diisocyanate, hexamethylene diisocyanate trimethyl-hexamethylene diisocyanate, isophoron diisocyanate, naphthylene diisocyanate and the like. The cycloaliphatic diisocyanate are preferred and the compound methylene bis(4-cyclohexyl isocyanate) is the most preferred of the isocyanates set forth above.

This intermediate reaction product is then reacted with an hydroxyl containing acrylic compound such as, for example, 2-hydroxyethylacrylate, 2-hydroxyethylmethacrylate, hydroxymethylacrylate, hydroxymethylmethacrylate, 3-hydroxypropylacrylate and 3-hydroxypropylmethacrylate.

A major disadvantage of prior art orthodontic bracket adhesive compositions are their susceptibility to brittle fracture, particularly in the area of the bond between the adhesive and the stainless steel mesh bracket base. The typical prior art adhesive formulation consists of a cured blend of filled dimethacrylate and/or monomethacrylate resins which is non-ductile and given to high crack propagation rates. This characteristic reduces impact resistance of the bond between the orthodontic bracket and tooth as well as the ultimate tensile or shear load. Attempts to improve adhesive ductility by plasticizing the resin blend also weaken the resulting polymer. Known compositions after cure exhibit approximately the following mechanical properties.

| | |
|---|---|
| compressive strength* | 100–190 MPa |
| modulus of elasticity* | 200 MPa |
| gel time (23° C.)* | 90–150 sec |
| shear bond strength mesh-base bracket to etched extracted tooth | 120–180 Kg/cm$^2$ |

*determined according to Specification No. 27 described in Journal of the American Dental Assc., Vol., 94 (June 1977)

Compositions with the properties given above and based on blends of acrylic or methacrylic monomers are available in three forms; (1) two paste adhesives, which are mixed prior to use to initiate polymerization and are typically used with a two part sealant which is generally an unfilled or low viscosity form of the adhesive resin blend; (2) so-called no-mix adhesives in which polymerization is initiated when the filled adhesive blend is brought into contact with a liquid or paste activator and (3) light-cured adhesive in which polymerization of a single paste adhesive containing a light sensitive polymerization initiator is caused by irradiation of the material by UV or visible light.

It has been found that the elastic properties of existing compositions can be improved, that is the modulus of elasticity reduced without effecting other desired mechanical properties by the use of the monomers of the present invention.

The adhesive compositions of the present invention contain at least one of the monomers of the present invention, a polymerization initiator or accelerator and may contain typical additives such as additional monomers, fillers-both organic and/or inorganic, UV absorbers, stabilizers, dyes, etc. The trimethacrylate monomers of this invention may be combined with other polymerisable unsaturated materials such as acrylic or methacrylate monomers, or oligimers and polymerized or cured at the time of use.

DETAILED DESCRIPTION OF THE INVENTION

In order to obtain the desired physical and mechanical properties for use as a dental adhesive, the compound of the present invention is preferably mixed with one or more suitable monomers in a concentration of about 5 to 95 percent by weight of the monomer mix. Such monomers are generally well known in the art and include one or more polymerizable acrylates and/or methacrylates. Typical of such additions are alkanediol dimethacrylates; and reaction products of bisphenols, in particular bisphenol A and glycidyl methacrylate, hereinafter Bis/GMA. Specifically such materials can be ethylene glycol dimethacrylate; di-, tri-, or tetraethylene glycol dimethacrylate; 1,4-butanediol dimethacrylate; 1,6-hexanediol dimethacrylate, trimethyol propane trimethacrylate, and ethoxylated bisphenol A dimethacrylate. Naturally, the foregoing list is exemplary only, and other known polymerizable compounds can be used for this purpose.

Filling materials may preferably be employed for reinforcing properties or to add body and flow control to the monomer blend. The fillers can be organic in nature or inorganic and may be present in any desirable concentration up to about 80% by weight of the adhesive composition. Generally inorganic fillers are preferred, and they may be transparent or opaque to X-rays. In particular silica-based materials have been found useful. Examples of satisfactory materials are barium alumino-silicate, boro-silicate glass, quartz, lithium alumino-silicate, fumed silica, and calcium silicate. The particle size of such fillers normally may be between about 0.01 and 50 microns. It is also useful to use combinations of fillers of very small and larger particle sizes. An example would be a combination of fumed silica with particle size range of about 0.01 to 0.1 micron and ground barium glass (barium aluminosilicate) of about 0.5 to 20 micron size range.

It has also been found that the flow control of adhesive compositions of the subject monomers may be enhanced by use of organic fillers such as poly(methacrylate), or copolymers thereof. These fillers can be employed either as dispersions of fine particles or may be dissolved.

The compositions of the present invention lend themselves to two basic forms one or two phase preparations. In the later case one phase will contain a polymerization initiator and the other will contain an accelerator for the initiator. Suitable initiators are typically organic peroxides, while the accelerators employed are generally organic amines. In these cases the two phases are brought together either just prior to bonding the bracket to a tooth, in the case of adhesive compositions that are generally known as a "two-paste adhesives", or on the tooth during the bonding operation, in the case of adhesive compositions that are known as "single paste", or "no-mix" adhesives. Polymerization occurs within a few minutes on the tooth, which has preferably been previously acid-etched to improve the bonding surface. The tooth may also have been coated with a sealant (an unfilled resin blend polymerized in the manner of the adhesive composition) which is designed to penetrate the enamel fissures produced by acid etching, but which allows for a chemical bonding with the bracket adhesive composition.

Single phase compositions polymerize by action of light such as UV, visible, or a combination of both. Such compositions contain a photopolymerization initiator and may contain an accelerator. The monomers of the present invention are suitable in both types of composition. Many suitable photopolymerization initiators are known in the art. Among suitable compounds are benzil and benzil derivatives, or dicarbonyl compounds such as 2,3 pentonedione. Preferably the initiator constitutes 0.01 to 5.0% by weight of the total composition. Accelerators used in these compositions may be amines such as dimethyl-p-toluidine and trialkyl-amines, or amines with copolymerizable functional groups such as diethylamino ethylmethacrylate. Such accelerators are preferably about 0.02 to 2% by weight of the total composition.

In the two phase embodiments of the invention, polymerization is initiated when the polymerization initiator is brought in contact with the accelerator immediately prior to or during the bonding operation.

The initiator is generally a peroxide. Suitable peroxides include benzoyl peroxide, t-butyhydroperoxide, cumene hydroperoxide and t-butyl perbenzoate. Preferably these should be used in the range of 0.01 to 5.0% by weight of the total composition.

The accelerators (sometimes called activators) used with the present invention are typically aromatic amines. Suitable accelerators include, dimethyl-p-toluidine, N,N bis(2-hydroxyethyl)-p-toluidine, and N,N,3,5 tetramethyl aniline. For best results these compounds should be used in the range of 0.01 to 5.0% by weight of the total composition. It has been found particularly useful to place the polymerization initiator in one of the two phases and the accelerator in the other phase.

The aforementioned compositions may optionally include small amounts of compounds such as UV stabilizers, polymerizable organosilicon compounds to improve adhesive between fillers and the resin blend, dyes to provide natural appearance, and inhibitors to surpress premature polymerization of the compositions. Useful organo-silicon compounds are methacryloyl alkyl trihydroxy silane or methacrlyoylalkyl trihydroxy silane of methacryoylalkyl trimethoxysilane. Several suitable UV stabilizers are based on derivatives of benzoauinone and are available under a variety of trade names such as Cyansorb UV-9 from American Cyanamid Corporation. Examples of suitable inhibitors are hydroquinone, the methyl ether of hydroquinone, and 2.6 di-t butyl hydroxytoluene.

The following examples describe certain embodiments of the present invention. It should be understood that these examples are provided only to illustrate the nature of the invention and should not be understood as limiting the scope of this invention as defined in the claims.

EXAMPLE 1

To a 1 liter round bottom 3-neck flask was added, 1.5 gm dibutyltin dilaurate (catalyst), 0.6 gms butylated hydroxytoluene (as a polymerization inhibitor) to 262 grams (1 mole) of Molecular Weight or methylene bis(4 cyclohexylisocyanate). To this solution was added 176 gms (0,4 mole) of the poly(oxypropylene) adduct of trimethyloylpropane, trade name Pluracol 440 (BASF Wyandotte), while maintaining stirring and a constant temperature of 30°-40° C. After completion of the addition the reaction mix was stirred for one hour at 30°-40° C. Then 142 gm (1.0 mole) of 2-hydroxyethyl methacrylate was added dropwise to the reaction intermediate under conditions identical to the polyol addition. The resulting yield was 565 gm (97%) of a white, waxy material identified by NMR as 1,2,3-tris[1"methacryoylethoxy-1'(4',4"methylene bis)-(cyclohexyl urethane)poly(oxypropylene)]trimethyloyl propane and associated oligimers.

EXAMPLE 2

The resin produced in Example 1 was mixed with dimethacrylate resins to form a master blend as follows:
   Methacrylic terminated urethane from Ex. 1: 35% wt.
   Bis/GMA: 10%
   Triethylene glycoldimethacrylate: 25%
   Ethoxylated bisphenol A dimethacrylate: 30%

The master blend was combined with appropriate additives to form a conventional two-paste orthodontic adhesive as follows:
Part A:
   55.3 gm: master resin blend
   1.1 gm: benzoyl peroxide (catalyst)
   0.2 gm: Cyansorb UV-9 (Amer Cyanamide), UV absorber
   26.2 gm: ground barium glass (−325 mesh)
   0.05 gm: butylated hydroxytoluene (BHT), inhibitor
   16.1 gm: fumed silica
Part B:
   54.1 gm: master resin blend
   2.6 gm: N,N bis(2 hydroxyethyl)-p-toluidine (polymerization activator)
   0.21 gm: Cyanasorb UV-9
   27.6 gm: ground barium glass (−325 mesh)
   15.6 gm: fumed silica When mixed in equal proportion by volume, parts A & B gel in 2 minutes at 23° C. and obtain a hard set within 4 minutes. The adhesive formed by the mix of parts A & B was used to bond conventional mesh-based orthodontic brackets to phosphoric-acid etched extracted teeth. Tensile and shear adhesive bond strength of the brackets so bonded was determined by testing with an Instron Universal testing machine. Shear strength was 280±46 Kg/cm$^2$ and tensile strength was $36\pm8.5$ Kg/cm$^2$. These values are equal to or higher than those typically recorded for conventional Bis-GMA based orthodontic/adhesive formulas. All of the sample tests (10) failed at the adhesive/enamel interface. Typically, about half of conventional Bis-GMA based adhesive samples will fail at the adhesive/mesh interface due to brittle failure.

Compressive test specimens of 4 mm diameter and 8 mm height were prepared from the adhesive mix and tested on the Instron tester. Compressive strength, ultimate was 179 mPa (vs. 100-190 mPa for typical Bis-GMA based materials) and modulus of elasticity was 98 mPa (vs. about 200 mPa for Bis/GMA materials). The results indicate that the methacrylate terminated urethane compound from Example 1 can flexibilize the resin binder without weakening the structure.

EXAMPLE 3

A "no-mix" version orthodontic adhesive was prepared from the master resin blend from example 2 as follows:
Adhesive Paste:
  master resin blend: 57.0 gm
  Cyansorb UV-9: 0.1 gm
  benzoyl peroxide: 0.2 gm
  BHT, inhibitor: 0.06 gm
  ground barium glass, filler: 29.3 gm
  fumed silica filler: 10.9 gm
Activator Solution
  Bis GMA: 50.0 gm
  triethylene glycol dimethacrylate: 50.0 gm
  n,n bis(2-hydroxyethyl)-p-toluidine: 10.0 gm
  BHT: 0.03 gm
  UV-9: 0.15 gm
  Poly(methylmethacrylate): 10.0 gm Bond samples were prepared using extracted teeth and conventional mesh-based stainless steel orthodontic brackets by first etching the teeth with a 37% solution of phosphoric acid for 90 seconds then rinsing and drying. A small amount of the activator solution was then applied to both the etched tooth surfaces and bases of the brackets. A small portion of the adhesive paste is then placed on the primed bracket bases and brackets are placed on the prepared teeth with a moderate amount of pressure. Initial set was achieved in 35 seconds at 23° C. After conditioning for 24 hrs at 37° C. in 100% humidity, bond strength values were $182\pm27$ Kg/cm$^2$ in shear and 43-11 Kg/cm$^2$ in tensile vs. 135 Kg/cm$^2$ in shear and 35 Kg/cm$^2$ tensile for a commercial Bis/GMA-based formulation. The mode of failure was entirely adhesive/tooth for the samples of this example vs. mixed for conventional prior art formulations.

EXAMPLE 4

To a two liter round bottom flask was added 0.60 gm dibutyltin dilaurate, 0.24 gm of butylated hydroytoluene as an inhibitor and 84 gms (0.5 mole) of hexamethylene diisocyanate. While maintaining the temperature at 25°-30° C., 68 gm (0.16 mole) the poly(oxypropylene) adduct of trimethoylpropane (Pluracol TP 440) was added dropwise with constant stirring. After the completion of the addition, the reactants were stirred an additional 30 minutes at 30° C. Then 72.9 gm (0.5 mole) of 2-hydroxyethyl methacrylate was added dropwise with constant stirring at 25°-30° C. Yield was 241 grams of a clear, viscous resin.

The above product was compounded into a master resin blend #2 as follows:

methacrylate terminated urethane from above: 40 gm
  Bis/GMA: 10 gm
  triethylene glycol dimethacrylate: 25%
  ethoxylated bisphenol A dimethacrylate: 25%

The master blend was combined with appropriate additives to form a two-paste orthodontic adhesive as follows:
Part A:
  10 gm: master resin blend #2
  5 gm: ground barium glass
  3 gm: fumed silica
  0.3 gm: N,N bis(2-hydroxyethyl)-p-toluidine
Part B:
  10 gm: master resin blend #2
  5 gm: ground barium glass
  3 gm: fumed silica
  0.2 gm: benzoyl peroxide When mixed in equal parts by weight, the mix of A & B would gel in 2-5 minutes at 23° C. and obtain a hard set in 5 minutes. When used to bond orthodontic brackets to extracted teeth by the method described in Examples 2 and 3 the shear bond strength was $298\pm52$ Kg/cm$^2$ compressive strength of cured mixed adhesive was 216 MPa and elastic modules 182 MPa.

EXAMPLE 5

A two paste orthodontic bracket adhesive was formulated as follows:
Part A:
  trimethacrylate terminated urethane from Example 4: 6.0 gm
  triethylene glycol dimethacrylate: 14.0 gm
  N,N bis(2-hydroxyethyl)-p-toluidine: 0.6 gm
  fumed silica filler: 7.0 gm
Part B:
  trimethacrylate terminated urethane from Example 4: 6.0 gm
  triethylene glycol dimethacrylate: 14.0 gm
  benzoyl peroxide: 0.4 gm
  fumed silica filler: 6.3 gm Parts A and B when mixed in equal parts by volume cured in 2.5 minutes forming a translucent polymer. When used to bond stainless steel mesh-based orthodontic brackets by the method given in Example 1, the adhesive bond strength was 145 Kg/cm$^2\pm42$ Kg/cm$^2$.

Other modifications and ramifications of the present invention would appear to those skilled in the art upon reading this disclosure. These are also intended to be within the scope of this invention.

What is claimed is:

1. A two-paste dental adhesive composition which comprises in weight percent:
Part A:
  at least 5% of a trifunctional methacrylate or acrylic terminated urethane resin of the following chemical structure:

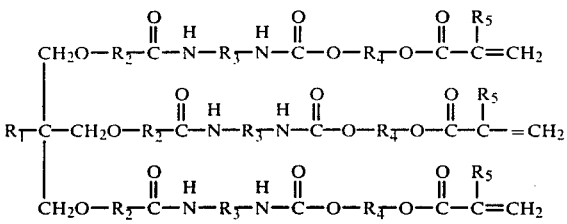

Where:
R$_1$ is —H, —CH$_3$, —CH$_2$CH$_3$ or —CH$_2$CH$_2$CH$_3$,
R$_2$ is (—CH$_2$CH$_2$—O—)$_n$ or

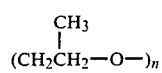

where: n=2 to 10,
R$_3$ is a divalent organic radical obtained by removal of two isocyanato groups from an organic diisocyanate,
R$_4$ is methylene, ethylene or propylene, and
R$_5$ is —H, or —CH$_3$,
blended with up to 95% of at least one polymerizable acrylate or methacrylate monomer, a catalyst, and a filler material; and Part B:
at least 5% of said trifunctional methacrylate or acrylic terminated urethane resin blended with up to 95% of at least one polymerizable acrylate or methacrylate monomer, a polymerization activator, and a filler material.

2. A two-component dental adhesive composition which comprises in weight percent:
Part A:
at least 5% of a trifunctional methacrylate or acrylic terminated urethane resin of the following chemical structure:

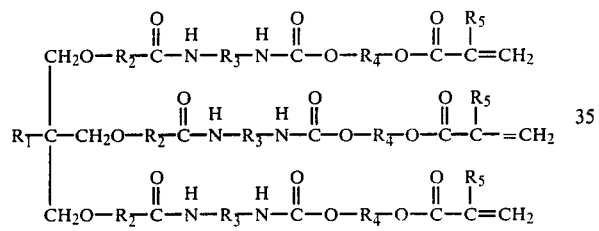

Where:
R$_1$ is —H, —CH$_3$, —CH$_2$CH$_3$ or —CH$_2$CH$_2$CH$_3$,
R$_2$ is (—CH$_2$CH$_2$—O—)$_n$ or

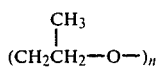

where: n=2 to 10,
R$_3$ is a divalent organic radical obtained by removal of two isocyanato groups from an organic diisocyanate,
R$_4$ is methylene, ethylene or propylene, and
R$_5$ is —H, or —CH$_3$,
blended with up to 95% of at least one polymerizable acrylate or methacrylate monomer, a catalyst, and a filler material; and Part B:
a solution which contains a polymerization activator.

3. A two-component dental adhesive composition which comprises in weight percent:
Part A:
at least 5% of a trifunctional methacrylate or acrylic terminated urethane resin of the following chemical structure:

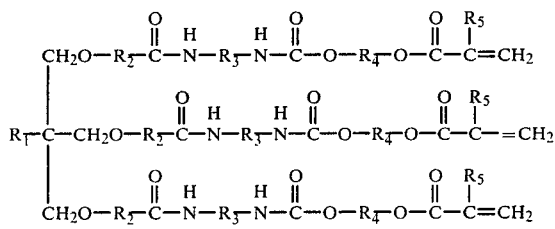

Where:
R$_1$ is —H, —CH$_3$, —CH$_2$CH$_3$ or —CH$_2$CH$_2$CH$_3$,
R$_2$ is (—CH$_2$CH$_2$—O—)$_n$ or

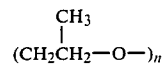

where: n=2 to 10,
R$_3$ is a divalent organic radical obtained by removal of two isocyanato groups from an organic diisocyanate,
R$_4$ is methylene, ethylene or propylene, and
R$_5$ is —H, or —CH$_3$,
blended with up to 95% of at least one polymerizable acrylate or methacrylate monomer, a polymerization activator, and a filler material; and Part B:
a solution which contains polymerization initiator.

* * * * *